United States Patent [19]
Stanworth et al.

[11] Patent Number: 5,955,076
[45] Date of Patent: *Sep. 21, 1999

[54] IMMUNOACTIVE PEPTIDES AND ANTIBODIES AND THEIR USE IN ANTI-ALLERGY TREATMENT

[75] Inventors: Denis Raymond Stanworth, Birmingham; Ian Victor Lewin, Tamworth; Sarita Nayyar, Wolverhampton; Valerie Jones, Gwynedd, all of United Kingdom

[73] Assignee: Peptide Therapeutics Limited, Cambridge, United Kingdom

[ * ] Notice: This patent is subject to a terminal disclaimer.

[21] Appl. No.: 08/480,379

[22] Filed: Jun. 7, 1995

Related U.S. Application Data

[62] Division of application No. 08/102,692, Aug. 5, 1993, abandoned, which is a continuation of application No. 07/776,380, filed as application No. PCT/GB90/00926, Jun. 15, 1990, abandoned.

[30] Foreign Application Priority Data

Jun. 15, 1989 [GB] United Kingdom .................... 8913737

[51] Int. Cl.$^6$ ........................ A61K 39/395; A61K 39/35; A61K 39/385; A61K 38/04
[52] U.S. Cl. ..................... 424/139.1; 424/145.1; 424/185.1; 424/193.1; 424/278.1; 530/327; 530/328; 530/350; 530/387.1; 530/388.22; 530/388.1; 530/389.1; 530/403; 530/806; 530/807; 530/810
[58] Field of Search ............................. 424/185.1, 139.1, 424/145.1, 193.1, 278.1; 530/387.9, 388.25, 389.1, 389.3, 807, 403, 328, 327, 387.1, 388.22, 388.1, 350, 806, 810

[56] References Cited

U.S. PATENT DOCUMENTS

| | | | |
|---|---|---|---|
| 4,161,522 | 7/1979 | Hamburger et al. | 424/177 |
| 4,223,016 | 9/1980 | Roy et al. | 424/177 |
| 4,579,840 | 4/1986 | Hahn | 514/14 |
| 4,683,292 | 7/1987 | Hahn | 530/328 |
| 5,283,243 | 2/1994 | Jasserand et al. | 514/224.5 |
| 5,601,821 | 2/1997 | Stanworth et al. | 424/139.1 |

FOREIGN PATENT DOCUMENTS

| | | |
|---|---|---|
| 0 287 361 | of 1988 | European Pat. Off. . |
| 2246780 | 2/1992 | United Kingdom . |
| WO 88/06040 | of 1988 | WIPO . |
| WO 89/04834 | of 1989 | WIPO . |

Primary Examiner—David Saunders
Assistant Examiner—F. Pierre VanderVegt
Attorney, Agent, or Firm—Nixon & Vanderhye

[57] ABSTRACT

An immunogen comprising a residue of a histamine-releasing peptide comprising a cationic N-terminal head and a hydrophobic C-terminal tail, together with a residue capable of eliciting antibodies against said peptide whilst inhibiting histamine release by said peptide is useful in anti-allergy treatment. Preferably the histamine-releasing peptide is of formula:

Lys-Thr-Lys-Gly-Ser-Gly-Phe-Phe-Val-Phe, optionally amidated at the C terminal.

Antibodies to the histamine-releasing peptide are useful for passive immunisation.

42 Claims, 2 Drawing Sheets

IMMUNOACTIVE PEPTIDES AND ANTIBODIES AND THEIR USE IN ANTI-ALLERGY TREATMENT

This is a divisional of application Ser. No. 08/102,692, filed Aug. 5, 1993, abandoned, which is a continuation of application Ser. No. 07/776,380, filed Nov. 26, 1991, now abandoned, filed as PCT/GB90/00926, Jun. 15, 1990, published as WO90/15878, Dec. 27, 1990, abandoned.

FIELD OF THE INVENTION

The present invention is directed towards the inhibition of interactions which would normally cause the release of histamine and other mediators between cell-bound IgE linked to an allergen and the cell.

DESCRIPTION OF THE PRIOR ART

Allergic symptoms are brought about through the release of vasoactive amines (mediators), notably histamine, from cells into the surrounding tissue and vascular structures. Histamine is normally stored in special cells known as mast cells and basophil leucocytes. The mast cells are dispersed throughout animal tissue whilst the basophils circulate within the vascular system. These cells manufacture and store histamine within the cell unless a specialised sequence of events occurs to trigger its release.

The role of immunoglobulin E (IgE) antibodies in mediating allergic reactions is well known. IgE is a complex arrangement of polypeptide chains which, as in other immunoglobulins consists of two light and two heavy chains linked together by disulphide bonds in a "Y" shaped configuration. Each light chain has two domains, one variable ($V_L$) domain linked to a domain with a relatively invariant amino acid sequence termed a constant domain ($C_L$). Heavy chains, by contrast, have one variable domain ($V_H$) and in the case of IgE, four constant domains ($C_H1$, $C_H2$, $C_H3$, $C_H4$, also known as Cε1, Cε2, Cε3, Cε4). The two "arms" of the antibody are responsible for antigen binding, having regions where the polypeptide structure varies, and are termed Fab' fragments (fragment-antigen-binding) or F(ab')2 which represents two Fab' arms linked together by disulphide bonds. The "tail" or central axis of the antibody contains a fixed or constant sequence of peptides and is termed the Fc fragment (fragment-crystalline). The Fc fragment contains the antibody's biologically active sites which enable the antibody to communicate with other immune system molecules or cells by binding to their Fc receptors. Fc receptors are molecules which bind with high affinity and specificity to molecular active sites within immunoglobulin Fc regions. Fc receptors may exist as integral membrane proteins within a cell's outer plasma membrane or may exist as free "soluble" molecules which freely circulate in blood plasma or other body fluids. FIG. 1 of the drawings shows the structure of an antibody molecule and the location of the antigen binding sites (Fab' arms), the Fc fragment, and the active sites which includes the cell binding site.

Active sites, depending on their function, may already be exposed and therefore able to bind to cellular receptors. Alternatively, they may be hidden until the antibody binds to the antigen, whereupon the antibody may change in structure and subsequently expose other active sites which can then trigger a specific immune activity.

The allergic (immunologic) release of histamine within the organism from the mast cells and basophils can only occur under the following circumstances. An IgE molecule must lock onto or attach itself at its Fc end to the cellular Fc receptor site, thus securing the IgE molecule to the mast cell or basophil (FIG. 2a). The Fab' portions of the cell-bound IgE molecules must be cross-linked by a particular compatible antigen (the allergen). Should such an interaction occur (FIG. 2b), the mast cell or basophil is automatically triggered to release histamine to the local environment, manifesting familiar allergic symptoms.

Conventional approaches to allergy treatment have involved systemic therapy with anti-histamines or attempts to desensitise patients, approaches which have not addressed themselves to the basic IgE-mast cell/basophil interaction.

Other prior art has concerned itself with the production of polypeptide chains capable of blocking the binding of the IgE antibody to the Fc receptors on the cell surfaces and displacing IgE from binding sites upon which IgE is already bound (FIG. 3).

Investigations have been carried out in order to define the nature of the "effector" site within the IgE Fc region thought to provide the immunological signal resulting in mast cell/basophil histamine release.

Structure-activity studies carried out on the model histamine-releasing polypeptides corticotrophin (ACTH) and melittin and analogues thereof indicated that a cluster of basic amino acids occurring in both these polypeptides was an essential requirement for the direct triggering of histamine release from rat peritoneal mast cells, [Jasani, B. and Stanworth, D. R., Int. Archs. Allergy Appl. Immun., 45. pp. 74–81 (1973) and Jasani, B. et al., Biochem. J., 181. pp. 623–632 (1979)]. Furthermore, the presence of neighbouring hydrophobic residues and the amidation of the C-terminal carboxylic acid residue were found to enhance triggering of this histamine release.

Based on these observations, the Fc region of human IgE, the structure of which had been elucidated [Bennich, H. and Bahr-Lindastrom, H. von, Prog. Immunol., 11, pp. 49–58 (1978)] was examined for amino acid sequences which fulfilled such criteria. The sequence spanning residues 496–506 within the Cε4 domain:

Arg-Lys-Thr-Lys-Gly-Ser-Gly-Phe-Phe-Val-Phe (all sequences in this specification are to be read in the normal way, i.e. with N-terminal at the left-hand end, C-terminal at the right-hand end) seemed the most likely to meet these structural requirements [Stanworth, D. R., et al., Biochem. J., 180, pp. 665–668 (1979)]. Consequently, peptides of various lengths composed of sequences representative of this region were synthesised and tested for an ability to induce non-cytolytic release of histamine from rat peritoneal mast cells in vitro. An octapeptide (sequence 497–504), nonapeptide (sequence 496–504) and a decapeptide (sequence 497–506) all showed dose-dependent histamine release over a concentration range of 0.100 $\mu$M.

As a result of these systematic studies, a picture emerged of the essential structural requirements for direct mast cell triggering and hence that part of the cell-bound IgE antibody molecules which provides a triggering signal as a consequence of their cross-linking by allergen. This structure comprises an N-terminal (cationic) polar head (e.g. Lys-Thr-Lys) separated by "indifferent" residues (e.g. Gly-Ser-Gly) from a hydrophobic C-terminal "tail" (e.g. Phe-Phe-Val-Phe-$NH_2$). (As usual, throughout this specification, the final $NH_2$ group shown means that the C-terminal carboxylic acid group has been amidated). Significantly, strikingly similar primary structural features were seen in the neuropeptide "Substance P".

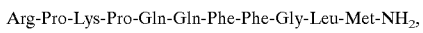

which when released from neurones, appears to act directly on neighbouring mast cells resulting in the release of histamine.

Stanworth et al. have suggested that there is a "second receptor" on the cell surface involved in the trigger of histamine (mediator) release. It has been hypothesised that the active sites of the Fc region of the IgE contain an "effector site" which is distinct from the site at which the IgE binds to the target cell (cell binding site). Following the cross linking of cell bound IgE with the antigen (allergen) a secondary mechanism is activated by the "effector site" (having the necessary trigger sequence of a cationic "head" separated by "indifferent" residues from a hydrophobic "tail"). It was suggested that when the allergen is bound to the cell bound IgE antibody, a change in conformation of the IgE occurs, bringing the IgE active sites into connection with a postulated "second receptor" on the cell surface membrane. The trigger of histamine release by the specific amino acid sequence (the "effector site") within the active sites was thought to occur by the insertion into the cell membrane lipid bilayer of the hydrophobic "tail", while the cationic "head" interacts with the supposed "second receptor" on the cell membrane [Stanworth, D. R. et al., Molec. Immunol. 21, pp. 243–247 (1984)]. The above explanation for the mechanism of histamine release from mast cells is not universally accepted. The prior art has concerned itself with the development of "blocking peptides" for the prevention of the binding of IgE to mast cells and basophils. The development of "anti-binding site antibodies", has elucidated this binding site and subsequently, blocking anti-peptides were developed [Burt, D. et al., Molecular Immunology., 24, pp. 379–389 (1987)]. However, it is known that the IgE antibody is often firmly bound to the mast cell or basophil [Stanworth, D. R., Nature 23, pp. 310–316 (1971)], even without the presence of an allergen, and it is only when the allergen is present that the supposed "second receptor" is triggered and the histamine is released.

Thus, merely blocking the site at which IgE binds to the mast cells would inhibit IgE function of only those IgE molecules which freely circulate and are not yet attached to the mast cells or basophils. This approach would be unsuitable where cell-bound IgE is already present, unless such a blocking peptide is also able to displace already bound IgE. This approach was taken by Hamburger who reported that a pentapeptide from the $C_H2$ domain of human IgE was capable of competing with IgE specific binding sites on mast cells in human skin [Hamburger, R. N., Science, 189, pp. 389–390 (1975)]. This result could not however be confirmed by other investigators. [Bennich, H. H. et al, Int. Arch. Allergy Appl. Immunol., 53, pp. 459–468 (1977)].

Assuming the validity of the "second receptor" hypothesis, it is not clear how to prevent the interaction between the postulated "effector site" on the anaphylactic (IgE) antibody molecule and this "second receptor" on the cell surface. Presumably the cross linking of mast cell bound IgE antibody molecules by a specific antigen (allergen) induces a conformational change within their Fc regions bringing the "effector site" into close juxtaposition with the "second receptor". In this event, any attempt to block this interaction could encounter problems of steric hindrance in the region of the supposed effector site.

SUMMARY OF THE INVENTION

It has now surprisingly been found that it is possible to produce in vitro, or, even more surprisingly, elicit in vivo, an antibody to the "effector site" in the region of the Fc fragment of IgE, which will prevent the release of histamine when the cell bound IgE is cross-linked to its specific allergen, even when the IgE is present in the circulation, already bound by its Fc region to the mast cell or basophil.

Accordingly, the invention provides an immunogen comprising (consisting of or including) a residue of a histamine-releasing peptide comprising a cationic N-terminal head and a hydrophobic C-terminal tail, together with a residue capable of eliciting antibodies against said peptide whilst inhibiting histamine release by said peptide. This definition covers various polymeric and cross-linked forms of peptide and a conjugate comprising a carrier coupled to the peptide, in short any form which renders the peptide "non-self" and reduces its histamine-releasing function to an acceptably low level, preferably zero.

In a first use of the invention, the host is actively immunised against the trigger sequence of the Fc region of IgE by administering to the host an immunogenically effective amount of an immunogen as defined above. Although the peptides are the trigger to histamine release, it is surprising that they themselves can be presented so that they do not substantially mediate histamine release.

The invention also includes a ligand comprising an antibody domain specific for a histamine-releasing peptide defined above. This definition covers mono- and polyclonal antibodies, antigen-binding fragments thereof, e.g. Fab' or F(ab')2, hybrid antibodies and single-chain domain antibodies. For brevity, the term "antibody" is used hereinafter to refer to said ligand.

In a second use of the invention, the host is passively immunised against the aforementioned amino acid sequence of the Fc region of human IgE by administering to said host a histamine-release-inhibitory-effective amount of a ligand comprising an antibody domain specific for the above-defined histamine-releasing peptide. The most preferred monoclonal antibody from which humanised antibodies and Fab' fragments may be prepared is the subject of a patent deposit described below.

DESCRIPTION OF THE PREFERRED EMBODIMENTS

Figure 1:
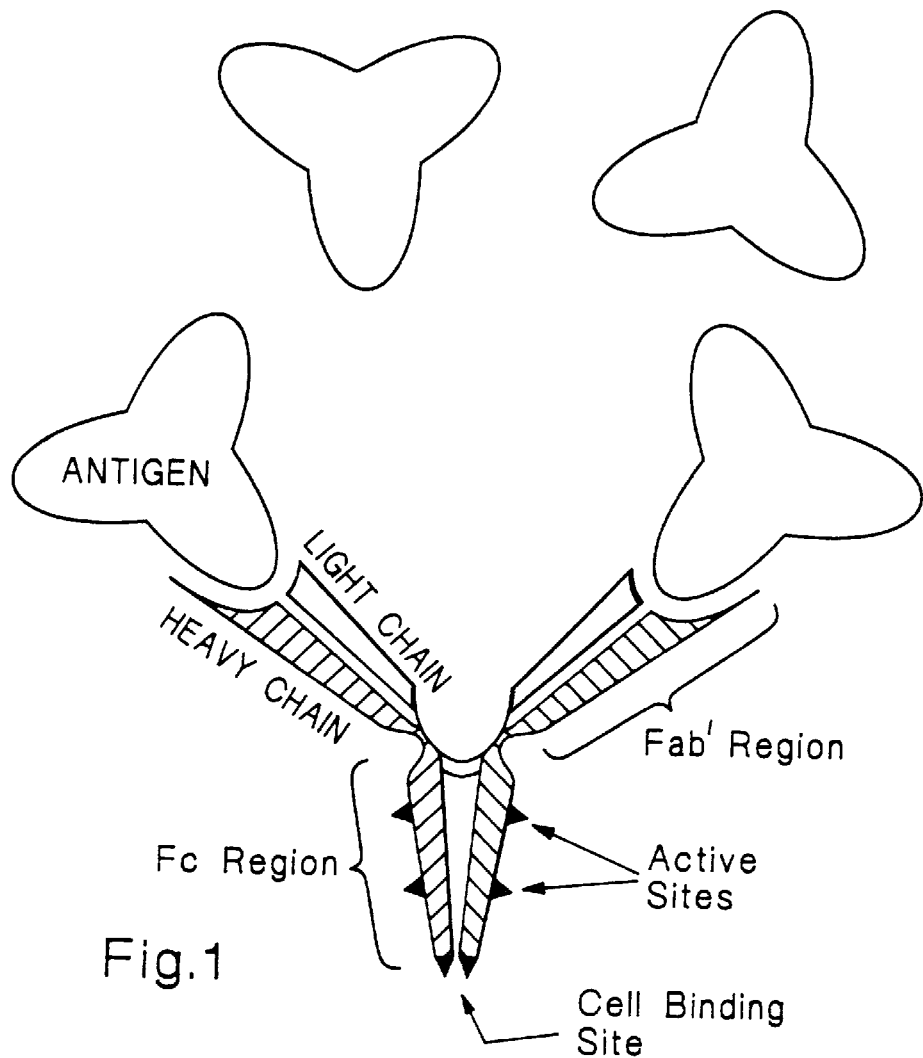
FIG. 1 shows the structure of an antibody and the location of the Fab' and Fc regions.
Figure 2A:
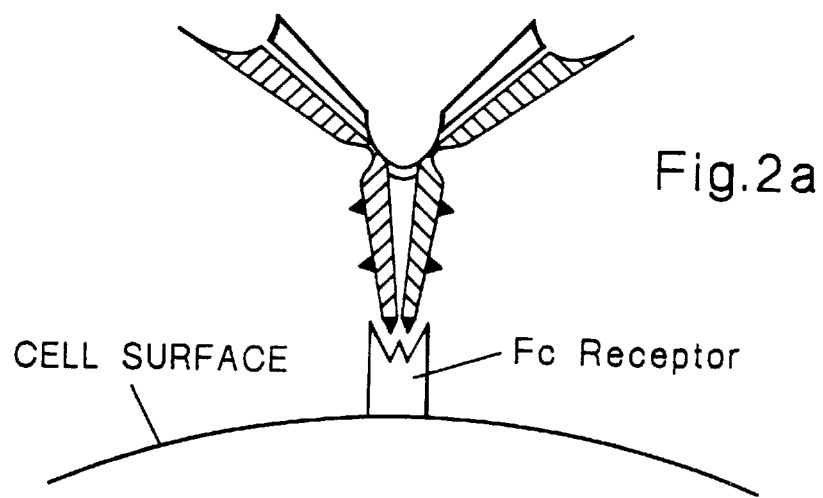
FIGS. 2a and 2b show the site at which the IgE antibody binds to the mast cell or basophil (2a) and how the cell-bound IgE antibodies cross link with antigen, exposing the "effector region" in the active sites of IgE which are able to approach the "second receptor" (2b).
Figure 2B:
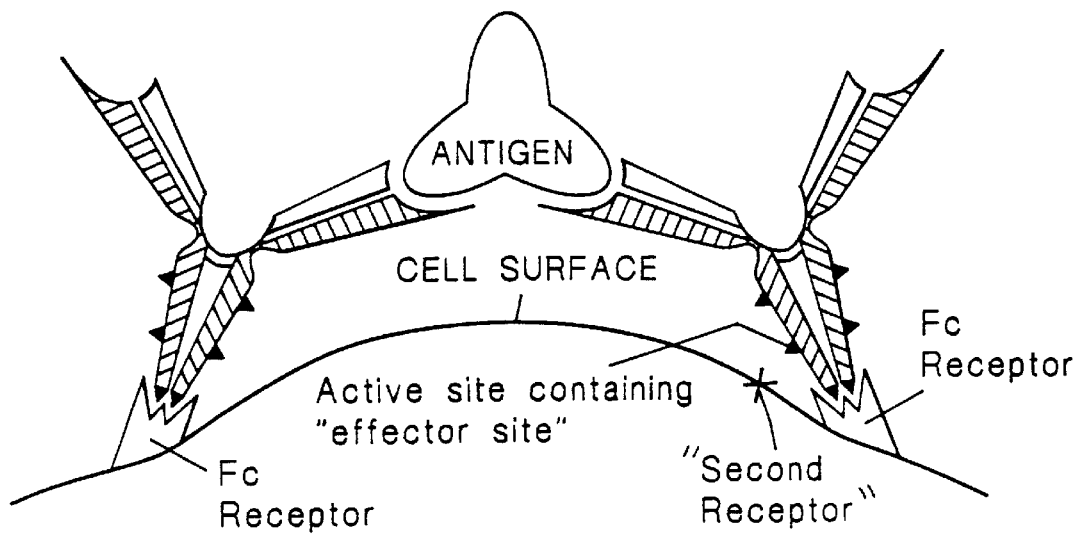
Figure 3:
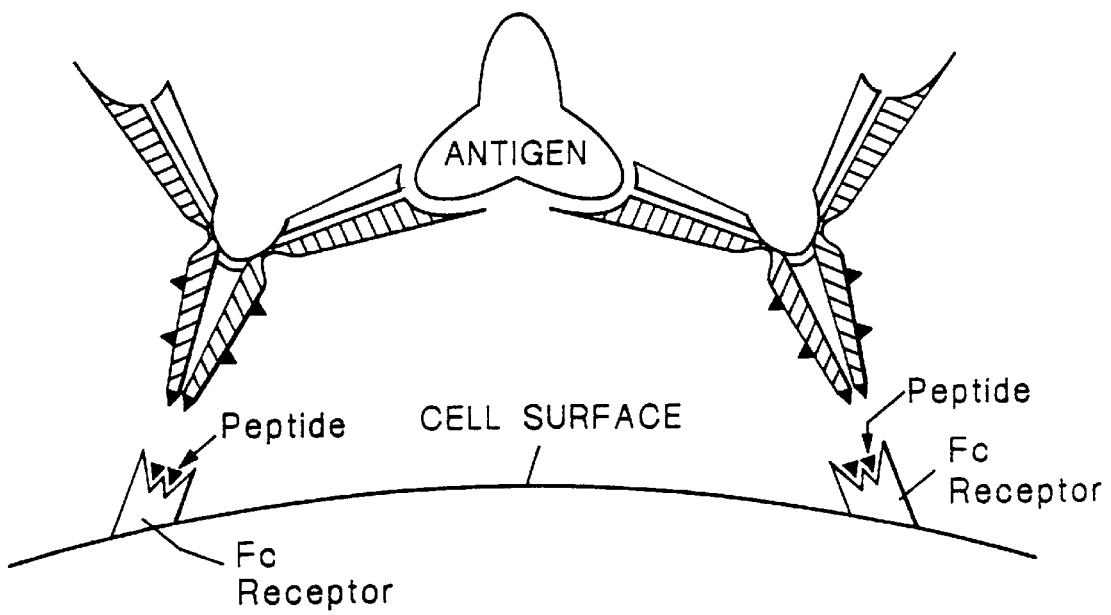
FIG. 3 shows the strategy of developing peptides to block IgE binding to the cell surface Fc receptor.

This invention is directed to inhibiting the release of histamine (mediator) from mast cells or basophils during an allergic reaction. This triggering stage occurs when a mast cell or basophil carrying surface-bound IgE is contacted with an antigen (allergen) for which the IgE is specific. The allergen binds to the surface-bound IgE, thereby producing a conformational change in the IgE, exposing the "effector sites" which interact with a "second receptor" on the surface of the cell to cause release of the histamine or other mediator stored within that cell.

This inhibition is brought about by interfering with the interaction between (1) the "active" sites in the Fc region of cell-bound IgE, which has become bound through its Fab' region with an allergen, thereby exposing the "effector" sites, and (2) the "second receptors" on the surface of the cell. (Normally, interaction between these "effector" sites and the "second receptors" would result in the release of histamine stored in the cell).

Immunisation may be passive, i.e. prophylactic treatment with at least the Fab' fragment of an anti-IgE amino acid sequence antibody, or, more preferably, active, i.e. inducing the host to produce its own antibodies, since active immunisation will provide a more effective and long lasting form of protection against immunologically triggered mediator release from IgE sensitised mast cells or basophils. Furthermore, there is evidence to suggest that the antipeptide antibody reduces the level of IgE production against an allergen (ovalbumin) in experimentally sensitised animals (rats).

The histamine-releasing peptide comprises a cationic N-terminal "head" and a hydrophobic C-terminal "tail". Preferably, the C-terminal tail is blocked by amidation. The N and C terminals will ordinarily be separated by a sequence comprising a number of "indifferent" amino acid residues which are predominantly non-polar and non-hydrophobic. The N and C-terminals are usually separated by from 2 to 8 amino acids, preferably 2 to 6, but more preferably by 3 amino acids. More preferably, the N and C terminals are separated by a Gly-Ser-Gly sequence. Proline and cysteine are not favoured.

The head must have a cationicity appropriate to the required interaction with the cell membrane at the "second receptor". Preferably it has a "double-top" of two cationic amino acid residues spaced apart, e.g. Lys-x-Lys where x represents at least one polar or neutral amino acid residue. The "head" will normally comprise the first one, two or three N-terminal amino acids. The tail has a hydrophobicity appropriate to its presumed entry into the lipid bilayer. It will normally comprise at least the final 2 amino acids, preferably the final 2 to 6 amino acids. The preferred amino acids for the tail are phenylalanine and tyrosine, but amino acids having extensive aliphatic side-chains such as valine, leucine or isoleucine can also be considered hydrophobic. The head or the tail can contain "indifferent" amino acids so long as they do not predominate and thereby cause loss of function. Most preferably the N-terminal head consists of either Lys alone or Lys-Thr-Lys and most preferably the C-terminal tail comprises a Phe-Phe sequence within the last four amino acids of the peptide.

Specifically preferred peptides include:

| | |
|---|---|
| Lys-Thr-Lys-Gly-Ser-Gly-Phe-Phe | (1) |
| Arg-Lys-Thr-Lys-Gly-Ser-Gly-Phe-Phe | (2) |
| Lys-Thr-Lys-Gly-Ser-Gly-Phe-Phe-Val-Phe | (3) |
| Lys-Thr-Lys-Gly-Ser-Gly-Phe-Phe-Val-Phe-Ser-Arg | (4) |
| Lys-Thr-Lys-Gly-Ser-Gly-Phe-Phe-Val | (5) | amidated derivatives thereof and amidated or non-amidated histamine-releasing analogues thereof. The decapeptide (3) is most preferred and the amidated version is hereinafter designated "F30".

These peptides mediate non-cytolytic release of histamine, but this release is inhibited when the peptide is conjugated to an immunogenic carrier material. Preferably the host will be "actively" immunised by administration of an immunogenic amount of a peptide which is substantially incapable of mediating histamine release, conjugated to an immunogenic carrier material, normally a protein. Conjugation can be via a short linking residue, e.g. via glutaraldehyde or a longer residue, e.g. of an amino acid, whereby the carrier is well spaced from the peptide. Such a linking residue must not interfere with the cationicity of the N-terminal head of the peptide residue. The peptides can be conjugated to the carrier via its C-terminal or N-terminal end.

Alternatively, the immunogen can take the form of a cyclic peptide containing the residue of the histamine-releasing peptide. Cyclisation seriously impairs histamine-release, as demonstrated in the Examples in which a cyclic peptide F40 is tested. This peptide is a cyclised form of F30 in which cysteine groups are added at each end of the non-amidated molecule. Some experimentation will be required to ensure that the cyclic peptide retains the fundamental histamine-releasing peptide in an appropriate conformation, but this is a simple matter of inserting spacing amino acids as required. In these cyclic peptides the cysteine-cysteine "bridge" residue constitutes the antibody-eliciting residue within the sense of the broadest definition herein of the immunogen of the invention.

The immunogen can take the form of a polymeric peptide in which the residue of one molecule of the peptide constitutes the "residue of the histamine-releasing peptide" in the broadest definition herein of the immunogen, and the remainder of the immunogen constitutes the antibody-eliciting residue within the sense of said definition. As shown in the Examples herein, dimerisation seriously impairs histamine release. Some experimentation may be required to determine the appropriate degree or form of polymerisation for the stimulation of the required antibodies.

The immunogens of the invention, while being substantially incapable of mediating non-cytolytic histamine release, are capable of eliciting antibodies with strong serological cross-reactivity with the target amino acid sequence of the Fc region of IgE.

The initial dose (e.g. 0.2–5 mg; preferably 1 mg.) of immunogen will be administered intra-muscularly, followed by repeat (booster) doses of the same 14 to 28 days later. Doses, of course, will depend to some extent on the age, weight and general health of the patient as is well known in the therapeutic arts.

The preparation of an antibody for "passive" immunisation can be carried out by administering the immunogen of the invention, preferably using an adjuvant, to mammals and collecting the resultant antiserum. Improved titres can be obtained by repeated injections over a period of time.

While there is no particular limitation to mammals provided for the preparation of antibodies, it is generally preferred to use rabbits or guinea pigs but horses, goats, pigs, rats, cows, sheep, etc., can also be used. In the production of antibodies, a definite amount of the antigen obtained as described above is diluted with a physiological saline solution to a suitable concentration and the resulting dilution is mixed with a complete Freund's adjuvant to prepare a suspension. The suspension is administered to mammals. For example, the aforesaid suspension is intraperitoneally administered (50 to 2,500 µg/time as the amount of the antigen) to rabbit. Then the suspension is administered every two weeks over a period of up to about 2–3 months, preferably about 1 month, to effect immunisation. The collection of the antibody is carried out by collecting blood from the immunised animal after the passage of 1 to 2 weeks subsequent to the final administration, centrifuging the blood and isolating serum from the blood.

The antibodies may include human and murine monoclonal antibodies. Preferably, the patient will be treated with an Fab' fragment preparation from the murine monoclonal antibody for a chimeric human-mouse antibody (comprising human Fc region and mouse Fab' region) so as to minimise any adverse reaction to the foreign animal immunoglobulin.

Murine monoclonal antibodies may be prepared by the method of Köhler and Milstein (Köhler, G. Milstein, C., Nature (London) 256, pg. 495 (1975)), e.g. fusion of spleen cells of hyperimmunised mice with a mouse myeloma cell line.

Human monoclonal antibodies are somewhat more difficult to raise, but, many methods have been utilised to raise human monoclonal antibodies, including:

(1) production of monoclonal antibodies by Epstein-Barr virus (EBV) transformed B-cells;

(2) cell line for B-lymphocyte hybridisation;

(3) human murine hybridomas;

(4) human-human hybridomas; and (5) human x human-mouse heterohybridomas.

Human x human-mouse heterohybridomas are the most preferred, and involve combining favourable characteristics of both human and murine parental cell types. Human-mouse heterohybridoma cell lines have been rendered suitable for B-cell fusion (Teng, N. N. M., Lam, K. S., Riera, F. C. and Kaplan, H. S., [Proc. Natl. Acad. Sci. U.S.A., 80, pg. 7308 (1983)].

The preferred monoclonal antibody from which the humanised antibodies can be constructed is the subject of a Budapest Treaty patent deposit, deposited on May 31, 1990 at the European Collection of Animal Cell Cultures, Porton Down, Salisbury, Wiltshire, England and given the accession number 90053107, and is hereinafter designated DEC 7B.

When used in the method of this invention, the antibody can be introduced into the host most conveniently by intramuscular injection. Any of the common liquid or solid vehicles may be employed, which are acceptable to the host and which do not have any adverse side effects on the host or any detrimental effects on the vaccine. Phosphate buffered saline (PBS), at a physiological pH, e.g. pH 6.8 to 7.2, preferably pH 7.0 may be used as a vehicle, alone or with a suitable adjuvant, such as an aluminium hydroxide-based adjuvant. The concentration of immunogenic antigen may very from about 50 to 500, preferably 200–300 µg per injection, in a volume of solvent generally of from about 0.25 to 1, preferably 0.5 ml. Multiple injections will be required after the initial injection and may be given at annual intervals.

Turning now to active immunisation, the term "immunogenic carrier material" herein includes those materials which have the property of independently eliciting an immunogenic response in a host animal and which can be covalently coupled to polypeptide either directly via a formation of peptide or ester bonds between free carboxyl, amino or hydroxyl groups in the polypeptide and corresponding groups on the immunogenic carrier material or alternatively by bonding through a conventional bifunctional linking group. Examples of such carriers include albumins of animal sera, globulins of animal sera, thyroglobulins of animals, haemoglobins of animals, haemocyanins of animals (particularly Keyhole Limpet Haemocyanin (KLH)), proteins extracted from ascaris (ascaris extracts, such as those described in Japanese Laid-Open Patent Application No. 16,414/81, J. Immun., 111, pp. 260–268 (1973), J. Immun., 122 pp. 302–308 (1979), J. Immun., 98, pp. 893–900 (1967) and Am. J. Physiol. 199 pp. 575–578 (1960) or purified products thereof); polylysine, polyglutamic acid, lysine-glutamic acid copolymers, copolymers containing lysine or ornithine, etc. Recently, vaccines have been produced using diphtheria toxoid or tetanus toxoid as immunogenic carrier materials [Lepow. M. L., et al., J. of Infectious Diseases, 150, pp. 402–406 (1984); and Coen Beuvery, E., et al., Infection and Immunity, 40, pp. 39–45 (1983)] and these toxoid materials can also be used herein. Other suitable carriers are disclosed in, for example, U.S. Pat. No. 4,575, 495, including vaccines, organic polymers, etc. The purified protein derivative of tuberculin (PPD) is particularly preferred for utilisation in the "active" immunisation scheme since (1) it does not induce a T-cell response itself (i.e. it is in effect a "T-cell hapten"), and yet it behaves as a fully processed antigen and is recognised by T-cells as such; (2) it is known to be one of the most powerful hapten "carriers" in the linked recognition mode; and (3) most importantly, it can be used in humans without further testing.

As hapten-carrier binding agents, those conventionally employed in the preparation of antigens can be widely employed.

The covalent coupling of the peptide to the immunogenic carrier material can be carried out in a manner well known in the art. Thus, for example, for direct covalent coupling it is possible to utilise a carbodiimide, most preferably dicyclohexylcarbodiimide or 1-ethyl-3-(3-dimethylaminopropyl) carbodiimide as coupling agent. Glutaraldehyde may also be used as a means of the covalent coupling of the peptide to the immunogenic carrier material.

In the above, proportions of the hapten, hapten-carrier binding agent and carrier can be appropriately determined but it is preferred that the carrier be employed in an amount of about 1 to about 6 times, preferably about 1 to about 5 times the weight of the hapten and the hapten-carrier binding agent be employed in an amount of about 5 to about 10 times the mol of the hapten. By the above reaction, the carrier is bound to the hapten via the hapten-carrier binding agent to obtain a desired antigen composed of a peptide-carrier complex.

After completion of the reaction, the thus obtained immunogen can easily be isolated and purified by means of a dialysis method, a gel filtration method, a fractionation precipitation method, etc.

Peptides used in the present invention may be readily synthesised by solid phase procedures well-known in the art. Suitable syntheses may be performed utilising "T-boc" or "F-moc" procedures.

Cyclic peptides are synthesised by the solid phase procedure employing the well-known "F-moc" procedure and polyamide resin in the fully automated LKB Biolynx apparatus.

The following Examples illustrate the invention.
"Tween" is a Registered Trade Mark.

EXAMPLE 1

Determination of Histamine-Releasing Capacity of Peptide (F30)-KLH Conjugate on Isolated Rat Mast Cells Rat peritoneal mast cells were prepared by washing out the peritoneum with cold $Ca^{++}$-free HBT buffer (Hepes-buffered Tyrode-Salt solution).

Hepes-buffered Tyrode—Salt Solution (X10 concentrated)

| | |
|---|---|
| NaCl | 137 mM |
| KCl | 2.7 mM |
| NaH$_2$PO$_4$.2H$_2$O | 0.4 mM |
| Glucose | 5.6 mM |
| MgCl$_2$.6H$_2$O | 0.5 mM |
| CaCl$_2$.2H$_2$O | 1 mM (not present in Ca++ free-HBT) |
| Hepes | 10 mM |
| Gelatine | 1 mg ml$^{-1}$ |

The above recipe was made up in 1 liter of distilled water and stored at −20° C. until use, whereupon it was diluted 1:10 and adjusted to pH 7.4 at 20° C. by addition of 0.2 M NaOH or 0.1 M HCl.

The cell suspension was centrifuged for 5 minutes at 1200 rpm and resuspended in HBT-Ca$^{++}$ buffer and washed again before finally being resuspended in 2 ml HBT-Ca$^{++}$ buffer. A small aliquot was stained with Alcian Blue and counted. The cells were used unpurified.

A synthetic human ε-chain decapeptide (designated F30) Lys-Thr-Lys-Gly-Ser-Gly-Phe-Phe-Val-Phe-NH$_2$ was coupled with glutaraldehyde to a carrier protein (Keyhole Limpet Haemocyanin (KLH), Sigma Chemical Co., Poole, Dorset). A series of tubes was set up containing 100 μl of serial dilutions of the F30-KLH conjugate from $10^{-8}$ to $10^{-4}$M (concentration of F30) and then an aliquot (100 μl) containing $10^5$ mast cells/ml was added to each tube. A similar series of dilutions was made with the F30 peptide in unconjugated form as a control.

The tubes were incubated for 30 min. at 37° C.; then 1 ml of cold HBT-Ca$^{++}$-free buffer was added to each tube and they were centrifuged at 2,000 rpm for 5 min. to stop the reaction. The supernatants were decanted into a matching set of tubes containing 0.25 ml 2M HClO$_4$ and 1.25 ml of 0.4M HClO$_4$ was added to the cell pellets to lyse them.

The percentage of histamine released from the mast cells was measured using a spectrofluorometric assay. The maximum releasing capacity of the peptide was greatly reduced when it was conjugated to KLH compared to that of free peptide.

The results are shown in Table 1.

TABLE 1

| PEPTIDE (F30) | % HISTAMINE RELEASE FROM RAT MAST CELLS EFFECTED BY | |
|---|---|---|
| CONCENTRATION | F30 | F30-KLH |
| 0 M | <10 | <10 |
| $10^{-8}$M | 15 | <10 |
| $10^{-7}$M | 10 | <10 |
| $10^{-6}$M | 15 | 10 |
| $10^{-5}$M | 50 | 15 |
| $10^{-4}$M | 70 | 22 |

EXAMPLE 2

Determination of Histamine Releasing Capacity of Peptides F30, F40 and F67 on Isolated Rat Mast Cells Three synthetic human ε-chain peptides, the amidated linear-unconjugated form (F30), an amidated dimerised form of this (F67) and a non-amidated, cysteine-bridged cyclic form (F40) were tested for their capacity to induce histamine release from isolated rat mast cells according to the method described in Example 1. As can be seen from the results in Table 2, both the cyclic (F40) and the dimerised (F67) forms showed appreciably less histamine release than the linear form (F30) although at the highest test dose ($10^{-3}$M), the F40 peptide was as active as the F30 peptide.

TABLE 2

| PEPTIDE | % HISTAMINE RELEASE FROM RAT MAST CELLS EFFECTED BY | | |
|---|---|---|---|
| CONCENTRATION | F30 | F40 | F67 |
| 0 M | 20 | 20 | 20 |
| $10^{-6}$M | 20 | 20 | 22 |
| $10^{-5}$M | 20 | 20 | 20 |
| $10^{-4}$M | 40 | 20 | 20 |
| $10^{-3}$M | 70 | 70 | 40 |

EXAMPLE 3

Production of Polyclonal (Rabbit) Antiserum Against Human ε-Chain Decapeptide (F30)

F30 was coupled to KLH or purified protein derivative (PPD) of tuberculin (Ministry of Agriculture, Fisheries and Food, Central Veterinary Labs., Weybridge), using glutaraldehyde as a coupling agent. The carrier protein (5 mg) and synthetic peptide (3 mg) were incubated with 21 mM glutaraldehyde (1 ml) for 2–3 hours at 4° C.

Female New Zealand white rabbits (3.5 kg, Buxted Rabbit Co.) were immunised by sub-cutaneous injection of peptide-carrier protein conjugate (250 μg) in complete Freund's adjuvant. Repeat sub-cutaneous injections in incomplete Freund's adjuvant, were performed at 14 and 28 days.

Test bleeds were taken 14 days after each injection, the anti-peptide antibody activity of the resultant sera being determined by direct and inhibition ELISA (Burt, D. S., Hastings, G. Z. and Stanworth, D. R., Molecular Immunology, 23, pp. 181–191 (1986)), employing 96-well flexible microtitre plates (Falcon, Cowley, Oxford). The optical density of each well was measured at 492 nm (OD492) in an automatic plate reader (Multiskan MC, Flow Laboratories, Irvine, Scotland) interfaced to a BBC Micro-Computer.

Specimen ELISA titration end-points shown by the rabbit polyclonal anti-peptide (F30) antiserum are given in Table 3.

TABLE 3

| | | ELISA READING OD492 | | | |
|---|---|---|---|---|---|
| SERUM DILUTION | NRS | Rabbit 1 | Rabbit 2 | Rabbit 3 | Rabbit 4 |
| Neat | 0.805 | 1.673 | 1.804 | 1.710 | 1.675 |
| 1:5 | 0.434 | 1.751 | 1.894 | 1.865 | 1.700 |
| 1:25 | 0.108 | 1.805 | 1.944 | 0.894 | 1.652 |
| 1:125 | 0.023 | 1.367 | 0.859 | 0.164 | 0.404 |
| 1:625 | 0.000 | 0.306 | 0.110 | 0.042 | 0.069 |
| 1:3125 | 0.000 | 0.054 | 0.003 | 0.013 | 0.005 |

NRS = normal rabbit serum.
Rabbits 1 and 2 were immunised with peptide (F30) - KHL conjugate.
Rabbits 3 and 4 were immunised with peptide (F30) - PPD conjugate.

EXAMPLE 4

Assessment of Anti-Allergy Activity of Rabbit Anti-Peptide (F30) Antiserum (a) In vitro Assays—Rat Peritoneal Mast Cell System In vitro assays were performed by determining the capacity of the polyclonal anti-peptide antiserum (F30) to inhibit the direct histamine release action of the human ε-chain decapeptide (F30) Lys-Thr-Lys-Gly-Ser-Gly-Phe-Phe-Val-Phe-NH$_2$ on rat mast cells, when presented together with the decapeptide.

Aliquots (150 μl containing approximately $10^4$ cells) of purified rat peritoneal mast cells, in Hepes buffered Tyrode solution (HBT) with added $Ca^{++}$ were incubated at 37° C. for 15 minutes in the presence of a mixture of equal volumes (100 μl) of decapeptide solution ($10^{-4}$ M) and rabbit antiserum (against peptide F30) diluted 1:4, 1:8 or 1:16. Afterwards, 650 μl of $Ca^{++}$-free HBT buffer was added and the suspension centrifuged (at approximately 500 g for 10 minutes), the amount of histamine released into the supernatant being determined by a standard automated spectrofluorimetric procedure.

Maximal (i.e. 90%) inhibition of peptide ($10^{-5}$M) induced histamine release was brought about using 1:4 dilution of rabbit polyclonal anti-F30 antiserum (as indicated in Table 4).

TABLE 4

| | INHIBITION OF F30 INDUCED HISTAMINE RELEASE BY POLYCLONAL ANTI-F30 ANTISERUM IN VITRO | |
|---|---|---|
| | HISTAMINE RELEASED % | INHIBITION % |
| Normal rabbit serum | 29.4 | 0 |
| Polyclonal anti-peptide antiserum diluted:- | | |
| 1:4 | 7.3 | 75 |
| 1:8 | 8.3 | 72 |
| 1:16 | 18.4 | 38 |

(b) In vivo Assays—Rat Passive Cutaneous Anaphylaxis (PCA) Inhibition Studies (i) Administration of rabbit anti-peptide (F30) antiserum with sensitizing allergic serum A mixture was made of equal volumes of rabbit anti-peptide (F30) antiserum and serum from a rat experimentally sensitised to ovalbumin. Aliquots (0.02 ml) of different dilutions of the mixture (i.e. neat, 1:2, 1:4, 1:8, 1:16 and 1:32) were injected intradermally into 2 male Wistar rats. After 48 hours, they were challenged by intrapenal injection of a mixture (0.25 ml of each) of ovalbumin solutions (20 μg/ml) and Evan's blue solution (1%). The animals were sacrificed at 1.5–2.0 hours, and their skins were removed and examined from the underside.

The blueing (PCA) reactions were measured and compared to those produced in 2 control animals similarly injected with a mixture of sensitised rat serum and normal rabbit serum. The blueing reactions were considerably reduced as indicated by the PCA scores in Table 5.

TABLE 5

| DILUTION OF SERA- | PCA SCORE SERUM ADMINISTERED WITH SENSITISING (ANTI-OVALBUMIN) SERUM | |
|---|---|---|
| MIXTURE ADMINISTERED | ANTI-PEPTIDE ANTISERUM | NORMAL RABBIT SERUM |
| Neat | 2 | 3 |
| 1:2 | 0 | 3 |
| 1:4 | 0 | 1 |
| 1:8 | 0 | 0.5 |

(ii) Administration of rabbit anti-peptide (F30) antiserum (a) with or (b) two minutes prior to or (c) two minutes after the challenging allergen (ovalbumin)

Rats (Wistar) were injected intradermally with different dilutions (neat, 1:2, 1:4, 1:8 or 1:16) of serum from a rat experimentally sensitized to ovalbumin. After 48 hours, one group (a) were injected intrapenally with a mixture (1:1) of equal volumes (0.25 ml) of ovalbumin (20 μg/ml) in Evan's blue (2%) and rabbit anti-peptide (F30) antiserum, and another group (b) were injected intravenously with rabbit anti-peptide (F30) antiserum (0.25 ml) 2 minutes prior to intravenous injection with 0.25 ml of a mixture (1:1) of ovalbumin (20 μg/ml) in Evan's blue (2%). A third group of rats (c) were injected intravenously with rabbit anti-peptide (F30) antiserum (0.25 ml) 2 minutes after intravenous injection with 0.25 ml of a mixture (1:1) of ovalbumin (20 μg/ml) and Evan's blue (2%). The animals were sacrificed at 1.5–2.0 hours, and their skins were removed and examined from the underside.

The results obtained are summarised in Table 6 in which the intensity of the blueing (PCA) reaction observed at each site has been "scored" by a ±system.

TABLE 6

| EXPERIMENTAL PROTOCOL | PCA RESPONSE OBSERVED AT THE SKIN SITE INJECTED WITH RAT SERUM SENSITISED TO OVALBUMIN DILUTED | | | | |
|---|---|---|---|---|---|
| | Neat | 1:2 | 1:4 | 1:8 | 1:16 |
| a | 5.00 | 3.00 | 0.75 | 0.25 | 0.00 |
| b | 5.30 | 4.00 | 0.75 | 0.00 | 0.00 |
| c | 6.00 | 4.75 | 2.25 | 0.75 | 0.00 |
| control | 6.00 | 4.25 | 3.00 | 1.75 | 0.25 |

The control was the administration of polyclonal anti-F02 (γ-chain) peptide in place of anti-F30 peptide.

As will be noticed from these figures, administration of the rabbit anti-peptide antiserum (as opposed to normal rabbit serum) brought about a reduction in the blueing reactions at sites injected with the various dilutions of sensitising serum; the inhibition was more marked in those passively sensitised rats which received the rabbit anti-peptide antiserum simultaneously with the challenging antigen (group a) than those (group b) which received the anti-peptide antiserum before-hand or group (c) which received the anti-peptide antiserum after the challenging antigen.

EXAMPLE 5

Active Immunisation with Human ε-Chain Decapeptide (F30) using CFA and IFA used as Adjuvants and its Influence on the State of Hypersensitivity of Experimentally Sensitised Rats (a) Sensitisation Procedure Groups of rats (male, Wistar) were hypersensitized by subcutaneous injection of a mixture (0.5 ml) of 0.5 ml chicken egg white (200 mg protein) and 2.5 ml *Bordetella pertussis* (40×10$^{10}$ organisms/ml) by a well-established experimental procedure (Jasani, B. and Stanworth, D. R., Journal of Immunological Methods, 30, pp. 55–68 (1979)). This resulted in the sensitization of their tissue mast cells by IgE antibody, and the appearance of high levels of ovalbumin specific IgE antibody in the circulation.

(b) Peptide Immunization Procedure

Groups of rats were immunised with the synthetic peptide F30-carrier protein conjugate (KLH or PPD), before or after their experimental sensitisation (as described in Example 3(a) above) according to the following protocol: first the animals were subcutaneously injected with a mixture (200 μl) of peptide-carrier protein conjugate (1 mg/ml) emulsified with an equal volume of complete Freund's adjuvant (CFA). Repeat subcutaneous injections of the peptide-carrier protein conjugate mixed with incomplete Freund's adjuvant (IFA) were administered at days 14 and 21.

(c) Assay of Immunised Rats' Sera (i) Anti-peptide (F30) response

Anti-peptide (F30) antibody activity associated with the major immunoglobulin isotypes, and with IgG subclasses, was determined by ELISA (enzyme linked immunoassay).

96-well flexible assay plates were coated with the F30 peptide. Aliquots (120 μl) of a 2.5 μM solution of the peptide were incubated for 1 hour at 37° C. The plates were then washed with 0.05% PBS (phosphate-buffered saline)/Tween buffer. Aliquots (100 μl) of the test rat sera, starting with a 1:4 dilution and double diluting thereafter were added to the F30 peptide coated plates. The plates were incubated for 1 hour at 37° C. Normal rat sera was used as a control. The plates were washed with 0.05% PBS/Tween buffer. 100 μl of goat-anti-rat IgG, IgM, IgA and IgE were added at a dilution of 1:1,000. The antibodies were diluted in 0.05% PBS/Tween buffer. The plates were incubated for 1 hour at 37° C. before being washed as above. Aliquots (100 μl) of rabbit-anti-goat IgG labelled with horseradish peroxidase diluted 1:1,000 with PBS/Tween were added to the plates and incubated for 1 hour at 37° C. The plates were washed as before, and 100 μl aliquots of substrate comprising 20 mg o-phenylenediamine, 250 μl H$_2$O$_2$ and 50 ml 0.15M citrate phosphate buffer pH 5.0 were added. The colour was allowed to develop for 5–15 minutes before the enzymatic colour reaction was stopped by the addition of 25 μl 4N H$_2$SO$_4$ to all wells. The optical density of the contents of each well was read at 429 nm (OD492) in a Titerek automated plate reader.

Typical results are shown in Table 7.

TABLE 7

| | Total anti-F30 IgG Maximum ELISA OD (OD492) | Histamine Release (ng/ml) in vaccinated rats on in vivo challenge with ovalbumin |
|---|---|---|
| CA 89 | 0.06 | 330 |
| A 89 | 0.75 | 70 |
| CB 89 | 0.03 | 2110 |
| B 89 | 0.33 | 200 |

A89: group of rats immunised with peptide-KLH conjugates before experimental sensitisation.
B89: group of rats immunised after experimental sensitisation.
CA89 and CB89 are the respective non-immunised control groups of rats.

(ii) IgE anti-ovalbumin response

The rats' IgE anti-ovalbumin (i.e. allergen) response was also determined by ELISA.

96-well flexible assay plates were coated with ovalbumin by incubation at 37° C. for 1 hour with aliquots (120 μl) of a 5 μg.ml solution of ovalbumin in PBS. After washing the plates with 0.05% PBS/Tween, 100 μl of test rat sera, starting with 1:4 dilution and double diluting thereafter, were added to the ovalbumin coated plates. The plates were then incubated at 37° C. for 1 hour. Normal rat sera was used as a control. After washing with 0.05% PBS/Tween, 100 μl of goat-anti-rat/IgG(Fc) were added to the plates at a dilution of 1:1,000 PBS/Tween. The plates were then incubated for 1 hour at 37° C. After washing with 0.05% PBS/Tween, aliquots (100 μl) of rabbit-anti-goat/IgG/horseradish-peroxidase were added at a dilution of 1:1,000 PBS/Tween and the plates were incubated at 37° C. for 1 hour. After incubation, the plates were washed as before. Aliquots (100 μl) of substrate were added, the substrate comprising 20 mg o-phenylenediamine, 250 μl H$_2$O$_2$ and 50 ml 0.15 M citrate phosphate buffer (pH 5.0). The colour was allowed to develop for 5–15 minutes and then the enzymatic colour reaction was stopped by addition of 25 μl of 4N H$_2$SO$_4$ to all wells.

The optical density of the contents of each well as read at 492 nm (OD492) in a Titertek automated plate reader.

Typical results showing the effect of pre- or post-sensitisation immunisation with human ε-chain decapeptide (F30) on circulating IgE anti-ovalbumin levels of rats experimentally sensitised to ovalbumin compared to IgE anti-ovalbumin levels of control (non-peptide immunised) experimentally sensitised rats are shown in Table 8.

TABLE 8

| 1:32 IgE DILUTION | OD492 |
|---|---|
| CA 89 | 0.548 |
| A 89 | 0.274 |
| CB 89 | 0.777 |
| B 89 | 0.644 |

A89: groups of rats immunised with F30-KLH conjugate before experimental sensitisation;
CA89: non-immunised controls;
B89: group of rats immunised after experimental sensitisation;
CB89: non-immunised controls.

(d) Appraisal of the Effect of Anti-peptide (F30) Antibody Production on the Rats State of Hypersensitivity Status The effect of pre- or post-sensitisation immunisation with peptide (as described in section (b) above) on the state of hypersensitivity of rats which had been experimentally sensitised to ovalbumin (according to Example 5(a) above) was determined by the following procedure; similar investigations were carried out on non-immunised groups of rats as a control.

Animals from both the immunized and control groups were bled (from the tail vein) prior to systemic allergen challenge by intrapenal injection of ovalbumin (5 mg). The animals were sacrificed 10 min. later, whereupon a further sample of blood was obtained from their hearts. The histamine levels in serum from both pre-and post-allergen challenge blood samples were determined by a standard automated spectrofluorimetric procedure; the antibody profiles of the sera being determined by ELISA (according to Example 5(c) above).

i. Effect of pre- or post-sensitisation immunisation with human ε-chain peptide (F30)

Pre-sensitisation immunisation of groups (of 6) rats with peptide-KLH conjugate results in a substantial reduction in the mean allergen-induced serum histamine level; as will be seen from the specimen data in Table 7 where the mean histamine levels recorded in the sera of the test animals was 70 ng/ml compared to a mean value of 330 ng/ml shown by the control group in response to allergen (ovalbumin) challenge.

Post-sensitisation immunisation of groups (of 6) rats with peptide-KLH conjugate brought about a much more dramatic reduction of the allergen induced histamine level; from a mean value of 2100 ng/ml in the control animals to 200 ng/ml in the test animals, the data is also shown in Table 7.

Rats which were immunised with peptide before or after sensitisation gave pronounced IgM and IgG (see Table 5) anti-peptide antibody responses in contrast to the control groups of rats; but no significant IgE anti-peptide antibody responses. Five out of six post-immunised rats who showed no signs of an adverse reaction to systemic allergen (ovalbumin) challenge, and no significant increase in their base line serum histamine levels, possessed high titres of IgG and IgM anti-peptide (F30) antibodies in their sera. A sixth immunised rat, which showed an increase in serum histamine level post allergen challenge, possessed no significant amounts of anti-peptide antibody in its circulation. In dramatic contrast, two of the control (non-peptide immunised) sensitised rats died from fatal anaphylactic shock two minutes after systemic allergen challenge.

Measurement, also of the pre- and post-immunised rats' IgE antibody responses against ovalbumin (i.e. the experimental allergen) compared to those of the control groups, revealed a significant decrease in the circulating IgE anti-ovalbumin levels resulting from pre-immunisation with the peptide (as indicated in Table 8).

ii. Effect of pre- or post-sensitisation immunisation with rat ε-chain dodecapeptide (F49) on a non-histamine releasing analogue (F57)

Similar pre- and post-sensitisation peptide immunisation studies on experimentally sensitised rats, to those described above, were performed employing as immunogen a rat ε-chain dodecapeptide F49 (Lys-Tyr-Asn-Gly-Ser-Asn-Gln-Arg-Phe-Phe-Ile-Phe-NH$_2$) or an analogue (F57) in which the N-terminal lysine residue is replaced by glycine.

Pre-sensitisation immunisation with peptide (F49)-PPD conjugate resulted in the mean allergen-induced serum histamine level being reduced to zero compared to a mean level of 300 ng/ml shown by the control group (of non-peptide immunised) rats; as is indicated in Table 9. Whilst post-sensitisation immunisation with the peptide-PPD conjugate brought about a reduction in allergen induced serum histamine level to 50 ng/ml from 950 ng/ml in the control animals. In contrast, pre- or post-immunisation of experimentally sensitised rats with the analogue (F57) of the rat ε-chain dodecapeptide (F49) had no significant effect on allergen-induced histamine release (as is also apparent from Table 7).

TABLE 9

| | HISTAMINE RELEASE ng/ml |
|---|---|
| Control A | 300 |
| F49A | 0 |
| F57A | 606 |
| Control B | 950 |
| F49B | 50 |
| F57B | 1159 |

A = Immunised with peptides before experimental sensitisation.
B = Immunised with peptides after experimental sensitisation.
F49 = Histamine releasing rat dodecapeptide.
F57 = Non-histamine releasing rat dodecapaptide F47 analogue.

EXAMPLE 6

Active Immunisation with Peptide (F30) using Al(OH)$_3$ and CP-20,961 as Adjuvants (a) Sensitisation Procedure Groups of rats were sensitised as described in Example 5(a).

(b) Peptide Immunisation Procedure—Al(OH)$_3$ used as an Adjuvant

Groups of sensitised rats were immunised with synthetic peptide (F30)-carrier protein conjugate (PPD used as a conjugate). The animals were subcutaneously injected with a mixture (200 μl) of peptide-PPD (1 mg/ml) emulsified in an equal volume of Al(OH)$_3$ adjuvant. This procedure was repeated on day 14. At day 35, tail bleeds were taken and the total anti-peptide antibody was measured by ELISA as described in Example 5(c).

The results are shown in Table 10.

TABLE 10

| | OD492 DILUTION OF SERUM | | | | | | | |
|---|---|---|---|---|---|---|---|---|
| RAT NO. | 1:2 | 1:4 | 1:8 | 1:16 | 1:32 | 1:64 | 1:128 | 1:256 |
| 1 | 0.10 | 0.20 | 0.40 | 0.50 | 0.55 | 0.50 | 0.45 | 0.30 |
| 2 | 0.45 | 0.55 | 0.70 | 1.00 | 1.10 | 1.10 | 1.00 | 0.79 |
| 3 | 0.60 | 0.65 | 0.85 | 0.90 | 0.95 | 0.75 | 0.65 | 0.40 |
| 4 | 0.65 | 0.95 | 1.00 | 1.00 | 1.00 | 1.00 | 0.80 | 0.40 |
| 5 | 0.75 | 0.90 | 0.95 | 1.05 | 1.40 | 1.45 | 1.50 | 1.20 |

(c) Peptide-immunisation Procedure—CP20,961 (Lipid Amine used as an Adjuvant

The immunisation of rats was carried out according to (b) above. 2 subcutaneous injections of peptide-PPD conjugate (500 μl) emulsified in CP 20,961 lipid amine adjuvant, on days 0 and 4. On day 35, tail bleeds were taken and total of the anti-peptide antibody was determined by ELISA. The results are shown in Table 11.

TABLE 11

| | OD492 DILUTION OF SERUM | | | | | | | |
|---|---|---|---|---|---|---|---|---|
| RAT NO. | 1:2 | 1:4 | 1:8 | 1:16 | 1:32 | 1:64 | 1:128 | 1:256 |
| 1 | 0.08 | 0.36 | 0.70 | 0.80 | 0.80 | 0.90 | 0.80 | 0.70 |
| 2 | 0.40 | 0.75 | 0.90 | 0.90 | 1.00 | 0.90 | 0.80 | 0.70 |
| 3 | 0.45 | 0.80 | 0.85 | 0.90 | 0.85 | 0.80 | 0.80 | 0.70 |
| 4 | 0.70 | 0.80 | 0.95 | 1.10 | 1.15 | 1.10 | 0.85 | 0.80 |
| 5 | 0.70 | 0.85 | 1.00 | 1.20 | 1.50 | 1.30 | 1.20 | 0.80 |

EXAMPLE 7

Production of Murine Monoclonal Antibodies (A) Immunisation

BALB/c mice were injected intraperitoneally (i.p.) with free peptide F30 (100 μg) or peptide F30 conjugated by glutaraldehyde treatment to a protein carrier (KLH or PPD) emulsified in equal volumes of Freund's complete adjuvant. Injections were repeated on day 14 and 28 with peptide or peptide conjugate emulsified in Freund's incomplete adjuvant. Test tail bleeds taken on day 28 or late were assayed for the presence of anti-peptide antibodies by indirect ELISA. Three days prior to fusion, mice showing raised serum antibody titres received a further booster injection (i.p.) of 100 μg peptide or peptide conjugate (100 ml) in an equal volume of PBS pH 7.2

(B) Fusion

Hyperimmunised mice were sacrificed by cervical-dislocation, their spleens removed and the cells isolated and washed. The spleen cells were fused with a mouse myeloma cell line (Ag. 8.653 or NSO/1) from a culture in logarithmic growth). By modification of the Köhler and Milstein method (Köhler, G. and Milstein, C., Nature (London) 256, pp. 495 (1975)), spleen and myeloma cells were fused at a ratio of 2:1 respectively, using 40% PEG (polyethylene glycol—mol. weight 1450). The fusion suspension was distrubuted into 96-well plates and cultured in medium containing HAT (hypoxanthine, aminopterin and thymidine).

After 10 days, plates were examined for growth of hybridomas. Supernatant removed from these cells was screened for the presence of anti-peptide antibodies by indirect ELISA.

(C) Cloning

When positive wells were identified as producing the desired antibody, the hybrid cells were cloned by limiting dilution and clones assayed again. Hybridomas may be cultured in flasks or grown in mice. Ascitic fluid was raised in BALB/c mice primed with pristane (0.5 ml injected i.p.) a few days prior to injecting with $10^6$–$10^7$ hybrid cells. Tumour formation should result after some 2–4 weeks and accumulated ascitic fluid removed by inserting a hypodermic needle into the abdominal cavity of the mouse. The concentration of monoclonal antibody in ascitic fluid was determined at every tumour passage, this may range from 5–15 mg/ml.

(D) Assay

Culture and ascitic fluids were screened for monoclonal anti-peptide (F30) antibody activity by indirect ELISA, using microtitre plates coated as described in Example 5(c) above (for the detection of rat anti-peptide antibodies). The second step involved incubating the plates for 1 hour at 37° C. with a 1:1,000 dilution of goat anti-murine IgG (total) labelled with peroxidase; followed by their development and reading in the standard manner.

Specimen ELISA data are provided in Table 12.

TABLE 12

| ASCITIC FLUID | ELISA READING (OD492) HYBRIDOMA CELL LINES | | | | |
|---|---|---|---|---|---|
| | DEC 1B | DEC 5A | DEC 6F | DEC 7B | DEC 4E |
| 1:40 | 1.597 | 1.322 | 1.693 | 1.068 | 1.305 |
| 1:80 | 1.567 | 1.327 | 1.473 | 1.102 | 1.235 |
| 1:160 | 1.557 | 1.395 | 1.329 | 1.087 | 1.092 |
| 1:320 | 1.475 | 1.295 | 1.218 | 0.994 | 0.922 |
| 1:640 | 1.266 | 1.192 | 1.025 | 0.642 | 0.713 |
| 1:1280 | 1.015 | 0.808 | 0.948 | 0.234 | 0.511 |
| 1:2560 | 0.630 | 0.681 | 0.910 | 0.140 | 0.300 |
| Hybridoma supernatant (1:4 dilution) | 1.342 | 0.923 | 1.020 | 1.355 | 1.079 |

We claim:

1. An immunogen comprising: i) a moiety consisting of a histamine-releasing peptide having a cationic N-terminal head and a hydrophobic C-terminal tail, and ii) a moiety capable of eliciting antibodies against said peptide while inhibiting histamine release by said peptide.

2. An immunogen according to claim 1 wherein the C-terminal of the peptide is blocked by amidation.

3. An immunogen according to claim 1 wherein the N-terminal head of the peptide comprises a Lys-Thr-Lys sequence.

4. An immunogen according to claim 1 wherein the N-terminal head of the peptide is separated from the C-terminal tail of the peptide by from 2 to 6 predominantly non-polar and non-hydrophobic amino acid residues.

5. An immunogen according to claim 4 wherein the N-terminal head of the peptide is separated from the C-terminal tail of the peptide by a Gly-Ser-Gly sequence.

6. An immunogen according to claim 1 wherein the histamine-releasing peptide has the sequence:

Lys-Thr-Lys-Gly-Ser-Gly-Phe-Phe-Val-Phe,     SEQ ID NO:6.

7. An immunogen according to claim 1 wherein the histamine-releasing peptide has the sequence selected from the group consisting of:

Lys-Thr-Lys-Gly-Ser-Gly-Phe-Phe,     SEQ ID NO:4

Arg-Lys-Thr-Lys-Gly-Ser-Gly-Phe-Phe,     SEQ ID NO:5

Lys-Thr-Lys-Gly-Ser-Gly-Phe-Phe-Val-Phe-Ser-Arg,     SEQ ID NO:7

Lys-Thr-Lys-Gly-Ser-Gly-Phe-Phe-Val,     SEQ ID NO:8 and amidated and non-amidated histamine-releasing analogues thereof.

8. An immunogen according to claim 1, in the form of a polymeric peptide in which a moiety of one molecule of the polymeric peptide constitutes said moiety of the histamine-releasing peptide and the remaining moiety of said molecule constitutes the antibody-eliciting moiety.

9. An immunogen according to claim 1, wherein the antibody-eliciting moiety comprises the moiety of a conjugate of the histamine-releasing peptide.

10. A composition for treatment of allergies comprising an immunogen according to claim 1 and an adjuvant.

11. A ligand comprising an antibody domain specific for a histamine-releasing synthetic peptide having a cationic N-terminal head and a hydrophobic C-terminal tail, said antibody domain being reactive also with the sequence of amino acids on the heavy chain of IgE which comprise the trigger signal for histamine release.

12. A ligand according to claim 11 in the form of monoclonal antibody.

13. A ligand according to claim 11 in the form of an Fab¹ or F(ab')₂ fragment of a monoclonal antibody.

14. An immunogen according to claim 1 wherein the hydrophobic C-terminal tail of the peptide comprises a Phe-Phe sequence and amino acids selected from the group consisting of Val, Leu and Ile.

15. An immunogen according to claim 1, wherein the N-terminal head of the peptide comprises a single Lys residue, the N-terminal head is separated from the C-terminal tail of the peptide by from 2 to 8 predominantly non-polar and non-hydrophobic amino acid residues and the C-terminal tail comprises a Phe-Phe sequence and has from 2 to 6 amino acid residues.

16. An immunogen according to claim 1 wherein the N-terminal head of the peptide comprises a Lys-Thr-Lys sequence, the N-terminal tail is separated from the C-terminal tail of the peptide by from 2 to 6 predominantly non-polar and non-hydrophobic amino acid residues and the C-terminal tail comprises a Phe-Phe sequence.

17. A method of anti-allergy treatment of a mammalian patient which comprises administering to said patient an amount effective to combat allergic reaction of an immunogen comprising i) a moiety consisting of a histamine-releasing synthetic peptide having a cationic N-terminal head and a hydrophobic C-terminal tail, and ii) a moiety capable of eliciting antibodies against said peptide whilst inhibiting histamine release by said peptide.

18. The method according to claim 17 wherein the C-terminal of the peptide is blocked by amidation.

19. A method according to claim 17 wherein the N-terminal head of the peptide comprises a Lys-Thr-Lys sequence.

20. A method according to claim 17 wherein the N-terminal head of the peptide is separated from the C-terminal tail of the peptide by from 2 to 6 predominantly non-polar and non-hydrophobic amino acid residues.

21. A method according to claim 20 wherein the N-terminal head of the peptide is separated from the C-terminal tail of the peptide by a Gly-Ser-Gly sequence.

22. A method according to claim 17 wherein the N-terminal head of the peptide comprises a Lys residue and the N-terminal head of the peptide is separated from the C-terminal tail by from 2 to 8 predominantly non-polar and non-hydrophobic amino acid residues.

23. A method according to claim 22 wherein the hydrophobic C-terminal tail of the peptide comprises a Phe-Phe sequence and amino acids selected from the group consisting of Val, Leu and Ile.

24. A method according to claim 17 wherein the N-terminal head of the peptide comprises a single Lys residue, the N-terminal head is separated from the C-terminal tail of the peptide by from 2 to 8 predominantly non-polar and non-hydrophobic amino acid residues and the C-terminal tail comprises a Phe-Phe sequence and has from 2 to 6 amino acid residues.

25. A method according to claim 17 wherein the N-terminal head of the peptide comprises a Lys-Thr-Lys sequence, the N-terminal tail is separated from the C-terminal tail of the peptide by from 2 to 6 predominantly non-polar and non-hydrophobic amino acid residues and the C-terminal tail comprises a Phe-Phe sequence.

26. A method according to claim 17 wherein the histamine-releasing peptide has the sequence:

| | |
|---|---|
| Lys-Thr-Lys-Gly-Ser-Gly-Phe-Phe-Val-Phe, | SEQ ID NO:6. |

27. A method according to claim 17 wherein the histamine-releasing peptide has a sequence selected from the group consisting of:

| | |
|---|---|
| Lys-Thr-Lys-Gly-Ser-Gly-Phe-Phe, | SEQ ID NO:4 |
| Arg-Lys-Thr-Lys-Gly-Ser-Gly-Phe-Phe, | SEQ ID NO:5 |
| Lys-Thr-Lys-Gly-Ser-Gly-Phe-Phe-Val-Phe-Ser-Arg, | SEQ ID NO:7 |
| Lys-Thr-Lys-Gly-Ser-Gly-Phe-Phe-Val, | SEQ ID NO:8 | and amidated and non-amidated histamine-releasing analogues thereof.

28. A method according to claim 17 wherein the immunogen is in the form of a polymeric peptide in which a moiety of one molecule of the polymeric peptide constitutes the said moiety of the histamine-releasing peptide and the remaining moiety constitutes the antibody-eliciting moiety.

29. A method according to claim 17 wherein the antibody-eliciting moiety of the immunogen comprises the moiety of a conjugate of the histamine-releasing peptide.

30. A ligand according to claim 11 wherein the C-terminal of the peptide is blocked by amidation.

31. A ligand according to claim 11 wherein the N-terminal head of the peptide comprises a Lys-Thr-Lys sequence.

32. A ligand according to claim 11 wherein the N-terminal head of the peptide is separated from the C-terminal tail of the peptide by from 2 to 6 predominantly non-polar and non-hydrophobic amino acid residues.

33. A ligand according to claim 32 wherein the N-terminal head of the peptide is separated from the tail of the peptide by a Gly-Ser-Gly sequence.

34. A ligand according to claim 11 wherein the hydrophobic C-terminal tail of the peptide comprises a Phe-Phe sequence and amino acids selected from the group consisting of Val, a Leu and Ile.

35. A ligand according to claim 11 wherein the N-terminal head of the peptide comprises a single Lys residue, the N-terminal head is separated from the C-terminal tail of the peptide by from 2 to 8 predominantly non-polar and non-hydrophobic amino acid residues and the C-terminal tail comprises a Phe-Phe sequence and has from 2 to 6 amino acid residues.

36. A ligand according to claim 11 wherein the N-terminal head of the peptide comprises a Lys-Thr-Lys sequence, the N-terminal tail is separated from the C-terminal tail of the peptide by from 2 to 6 predominantly non-polar and non-hydrophobic amino acid residues and the C-terminal tail comprises a Phe-Phe sequence.

37. A ligand according to claim 11 wherein the histamine-releasing peptide has the sequence:

| | |
|---|---|
| Lys-Thr-Lys-Gly-Ser-Gly-Phe-Phe-Val-Phe, | SEQ ID NO:6. |

38. A ligand according to claim 11 wherein the histamine-releasing peptide has the sequence selected from the group consisting of:

| | |
|---|---|
| Lys-Thr-Lys-Gly-Ser-Gly-Phe-Phe, | SEQ ID NO:4 |
| Arg-Lys-Thr-Lys-Gly-Ser-Gly-Phe-Phe, | SEQ ID NO:5 |
| Lys-Thr-Lys-Gly-Ser-Gly-Phe-Phe-Val-Phe-Ser-Arg, | SEQ ID NO:7 |

Lys-Thr-Lys-Gly-Ser-Gly-Phe-Phe-Val,      SEQ ID NO:8 and amidated and non-amidated histamine-releasing analogues thereof.

39. A method of anti-allergy treatment of a mammalian patient which comprises administering to said patient an amount effective to combat allergic reaction of the ligand claimed in claim 11, which is physiologically tolerable to the patient.

40. A method according to claim 39 wherein the N-terminal head of the peptide comprises a single Lys residue, the N-terminal head is separated from the C-terminal tail of the peptide by from 2 to 8 predominantly non-polar and non-hydrophobic amino acid residues and the C-terminal tail comprises a Phe-Phe sequence and has from 2 to 6 amino acid residues.

41. A method according to claim 39 wherein the N-terminal head of the peptide comprises a Lys-Thr-Lys sequence, the N-terminal tail is separated from the C-terminal tail of the peptide by from 2 to 6 predominantly non-polar and non-hydrophobic amino acid residues and the C-terminal tail comprises a Phe-Phe sequence.

42. A method according to claim 39 wherein the histamine-releasing peptide has the sequence:

Lys-Thr-Lys-Gly-Ser-Gly-Phe-Phe-Val-Phe,      SEQ ID NO: 6.

* * * * *